United States Patent
Brehmeier-Flick et al.

[11] Patent Number: 5,951,487
[45] Date of Patent: Sep. 14, 1999

[54] INTRACORPOREAL MEASURING SYSTEM

[75] Inventors: Bernd Brehmeier-Flick, Rinteln; Lorenz Runge, Hannover; Jens Krause, Garbsen, all of Germany

[73] Assignee: SICAN F&E GmbH (SIBET), Hannover, Germany

[21] Appl. No.: 08/931,332

[22] Filed: Sep. 16, 1997

[30] Foreign Application Priority Data

Sep. 20, 1996 [DE] Germany .................. 196 38 813

[51] Int. Cl.⁶ .................................................. A61B 5/00
[52] U.S. Cl. .................. 600/561; 600/486; 73/727
[58] Field of Search ................... 600/485, 486, 600/488, 561; 73/727

[56] References Cited

U.S. PATENT DOCUMENTS

| | | | |
|---|---|---|---|
| 3,724,274 | 4/1973 | Millar | 600/488 |
| 4,519,401 | 5/1985 | Ko et al. | 118/748 |
| 4,685,469 | 8/1987 | Keller | 600/488 |
| 4,722,348 | 2/1988 | Ligtenberg et al. | 128/675 |
| 4,738,267 | 4/1988 | Lazorthes et al. | 600/488 |
| 4,815,471 | 3/1989 | Stobie | 600/488 |
| 4,825,786 | 5/1989 | Beard | 600/488 |
| 5,207,103 | 3/1993 | Wise et al. | 600/488 |
| 5,263,244 | 11/1993 | Centa et al. | 29/832 |
| 5,715,827 | 2/1998 | Corl et al. | 600/486 |

FOREIGN PATENT DOCUMENTS 43 15 987  5/1993  Germany .

OTHER PUBLICATIONS

Lucas Nova®Sensor product brochure (1991).

*Primary Examiner*—Max Hindenburg
*Assistant Examiner*—Charles Marmor, II
*Attorney, Agent, or Firm*—Flehr Hohbach Test Albritton & Herbert LLP

[57] ABSTRACT

A Measurement device for medical applications is disclosed, comprising an intracorporeal sensor element (5), a extracorporeal evaluation unit and electrical connections (2, 6) between the sensor element (5) and the evaluation unit. The device comprises a flexible foil tape cable (1), which is intended for the electrical and mechanical connection of the evaluation unit with the sensor element (5) and a substrate (4), which is mechanically connected with the one end (3) of the foil tape cable (1) around the sensor element (1). The substrate (4) has an higher mechanical strength than the foil tape cable (1). The sensor element (5) is connected to electric cables (2) of the flexible foil tape cable (1) and the substrate (4) is enclosed with the sensor element (5) in a flexible mass (7).

4 Claims, 2 Drawing Sheets

INTRACORPOREAL MEASURING SYSTEM

In medical applications, measurement sensors are inserted into the body with the aid of a catheter (intracorporeal) and guided to positions where biosignals are to be measured. When measuring inside of the skull (intracranial), the sensors must have an extremely small cross-section. Therefore, semiconductor sensors are given preference, assembled and contacted in a carrier capsule.

For example, the cerebral pressure is measured by intracranial sensor measurement in the intensive care ward of the clinic for the diagnosis of hydrocephalus. The sensor is then removed and disposable sensors are destroyed, i.e. reusable sensors are sterilized and used on the next patient.

If, for example, a hydrocephalus is diagnosed, a so-called shunt system is applied. If the cerebral pressure increases above a certain limit, cerebral water (cerebrospinal fluid) is redirected to the peritoneal cavity, thus avoiding a dangerously high pressure in the brain.

The measurement of cerebral pressure can be made both epi- and subdural. Epidural means that the cerebral pressure can be determined indirectly between the hard meninge (dura mater) and the brain pan (calotte) by the pressure exerted by the cerebrospinal fluid on the meninge.

This measuring point has the advantage that the hard meninge is not penetrated, thus avoiding any infection of the meninge, the intervention is considerably more simple, no brain tissue is damaged during this intervention and the sensor can remain in measuring position for a longer period of time.

A subdural measurement means that the sensor is pushed beneath the and penetrates the meninge. This allows for the measurement of the pressure in the brain tissue (parenchyma). In frequent cases, the brain tissue is penetrated in order to allow for a measurement in the ventricle (intraventricular).

Various intracranial measurement systems are commonly familiar. For example, the firm B. Braun Melsungen AG offers an epidural measurement system under the name 'epidyn'. In this version, a semiconductor sensor is attached within a metal casing. The sensor is connected to strands of a cable, transmitting the electrical signals to an extracorporeal evaluation unit. This system has high manufacturing costs. Additionally, the minimum bending radius is no more than a few centimeters. If this radius is not achieved, then the danger is that these strands will break. However, medical applications require lesser bending radii, as the patients move around in bed and need to be washed.

Traditional pressure sensors involve the manufacturing of a metal case, into which the cable and the pressure sensor are pushed. In order to reduce the strain, the individual wires are wrapped around the pressure sensor, bonded with the pressure sensor and sealed with plastic. As a result of the small dimensions, this process can only be implemented with a lot of effort using tools of precision engineering.

In the U.S. Pat. No. 4,738,267, an implantable, intracranial pressure sensor is depicted, whereby electric cables are formed of cased strands in order to connect the sensor element with an extracorporeal evaluation unit. During production, these strands must be connected with each other in a laborious process. Additionally, there is the risk that the cable fibres will tear under strain and, the necessarily small bending radius mean that the strands may break.

In DE 43 15 987 C1, an extracorporeal body electrode is depicted, whereby a single sensor is attached to a flexible carrier foil. In order to connect an evaluation unit, a cable is attached to the end of the carrier foil using a clamp. The extracorporeal body electrode is only suited to measuring voltage and must not be given intracorporeal application. It would also not be suited to fulfil intracorporeal chemical, biological or physical sensory tasks.

In U.S. Pat. No. 5,263,244, a process for the manufacturing of a flexible semiconductor sensor arrangement for the optical pulse measurement is described. Integrated sensor elements are attached in a traditional manner to a flexible foil, fitted with electrically conductive tapes. The sensor elements, e.g. light-emitting diodes and photodetectors are connected with the conductive tapes using SMD engineering. The ends of the relatively short tapes are formed by contacts onto which the encased strands are soldered. This necessitates a fairly laborious soldering process, whereby the soldering points constitute a quality risk. Additionally, there is the risk that the strands break under tight bending radii. It is also not possible to solder integrated pressure sensors to the corresponding contacts on the conductive tapes using SMD engineering.

OBJECT OF THE INVENTION

The object of the invention was to create a measurement device for medical applications with an intracorporeal sensor element, an extracorporeal evaluation unit and electric connections between the sensor element and the evaluation unit. Furthermore, the system must be reliable, light and cost-efficient and must allow the patient to move around in bed.

The object was solved using the measuring system with the characteristics of claim 1. The manufacturing of the measurement system can take place simply and cost-effectively using the automatable process according to claim 6.

The invented measuring system can be produced at much less cost and has a greater tensile strength with a lower permissible bending radius. Movement and shearing of the sensor on the tape are compensated by the strengthening of the end of the foil with a plate-shaped substrate.

DESCRIPTION OF AN EMBODIMENT OF THE INVENTION

A cerebral pressure measurement system is to be presented as a preferred embodiment. Equally, the structural engineering can also be used for other medical applications.

Figure 1:
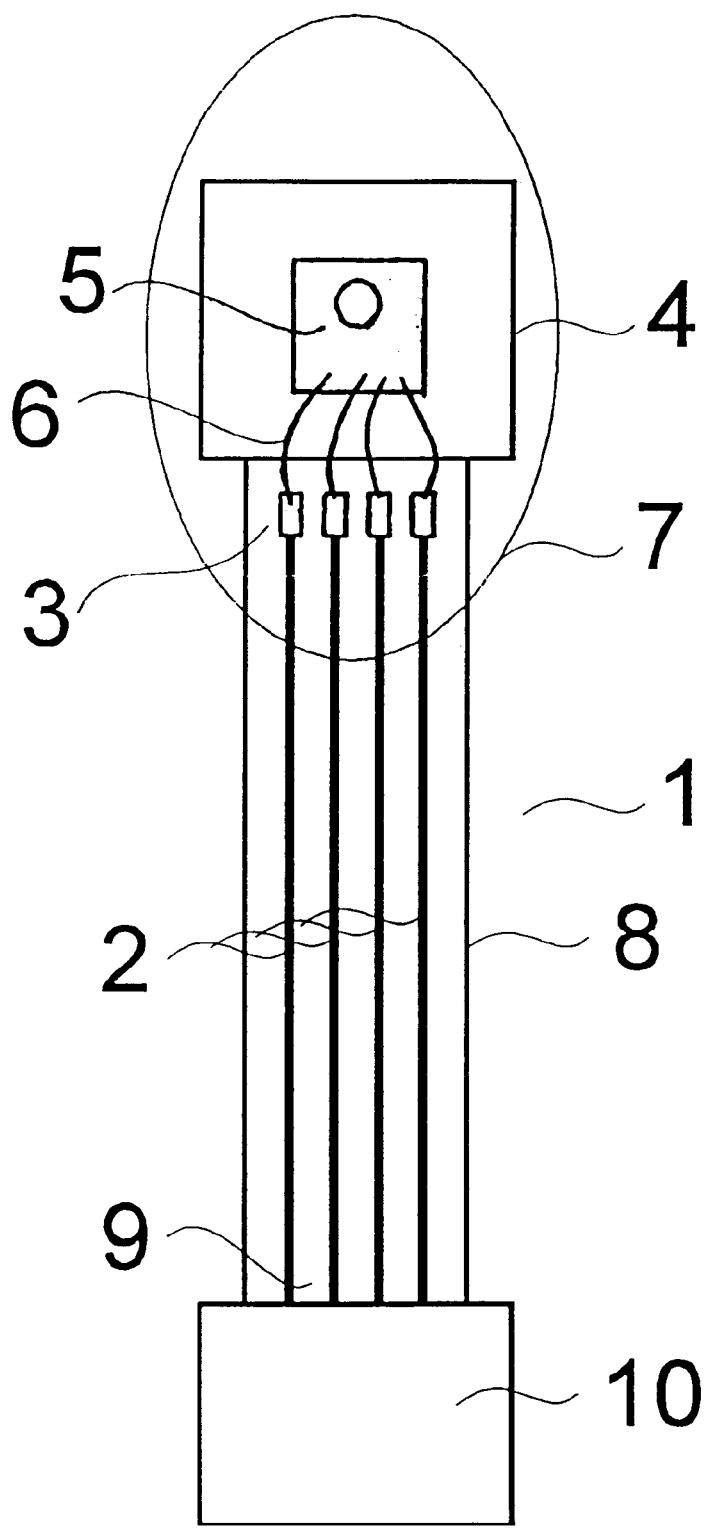
FIG. 1 is a top plan view of one embodiment of the invention.
Figure 2:
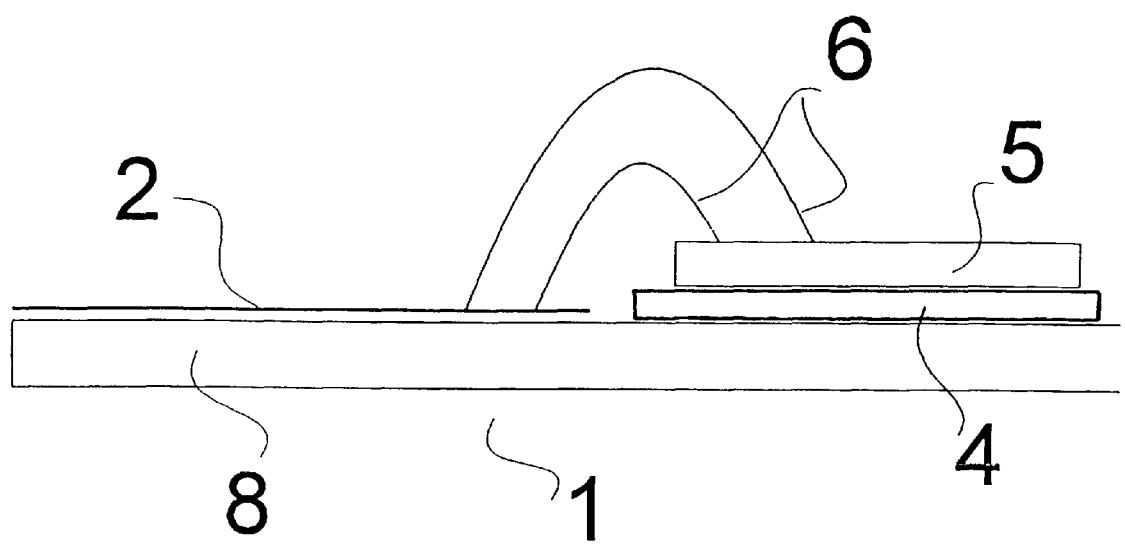
FIG. 2 is a fragmentary cross section view taken along the line 2—2 of FIG. 1.

FIGS. 1 and 2 depict an intracorporeal cerebral pressure measuring device. In order to replace the wires for energy supply and measurement signal transmission, a cable 3 is provided comprising a flexible tape 1 which carries a plurality of electrical tracks 2. At the end of the cable 3 there is a substrate 4 which strengthens the structural engineering of the sensor element. The pressure sensor 5 is attached to the substrate 4 and bonded with the connecting wires 6. After this, the bond wires of the pressure sensor 5 are fixed using a moulded mass 7. Subsequently, the pressure sensor 5 is moulded in a mass 7 made of polyumide or polyurethane. A silicon mass is given preference for this, as this is a flexible material through which pressure can be transmitted. Additionally, it offers sufficient insulation against electric current. This is particularly important for medical applications in order to protect the patient. The carrier material 8 of the flexible tape 1 is, e.g. a FR4 foil. The substrate 4 to strengthen the cable end 3 is currently made of a FR4 substrate. On the second contact end 9 of the flexible tape 1, there is a plug contact 10 or, in a further development, an electronic switch onto which the leveling switch is fitted.

In order to manufacture the tape cable 1, the carrier foil 8 is exposed, etched and stamped using traditional methods.

A plug contact 10 is attached to the second contact end 9. Alternatively, the electrical tracks 2 could be fanned out over the board with the evaluation switch then manufactured directly onto tape 1.

In order to carry out an intraventricular measurement of the cerebral pressure, the meninge is penetrated and the sensor 5 with the tape cable are fed into the ventricle through the brain mass. The ventricle is the part of the brain in which the cerebrospinal fluid circulation of the brain is closest to the spinal cord. In the even of a hydrocephalus, the ventricle is expanded and its discharge is occluded and impossible, thus meaning that the pressure there is a very exact and reliable indication for a disturbance of the circulation of the cerebrospinal fluid. The main advantage of an intraventricular cerebral pressure measurement is the high measurement exactness.

What is claimed is:

1. A measurement device for medical applications through connection with an extracorporeal evaluation unit, the measurement device comprising the combination of an intracorporeal sensor element (5), a flexible foil tape cable (1) comprising means for dried electrical and mechanical connection of the evaluation unit with the sensor element, said foil tape cable having a given mechanical strength, the foil tape cable further comprising an electrical track (2) between the sensor element and the evaluation unit, a substrate (4) mechanically connected with one end (3) of the foil tape cable, the substrate having a mechanical strength greater than said given mechanical strength of the foil tape cable, the sensor element being connected to said electric tracks (2) of the foil tape cable, and a flexible mass (7) enclosing both the substrate (4) and the sensor element (5).

2. Measurement device according to claim 1, characterised in that said substrate is comprised of a carrier material (8) and the foil tape cable (1) is made of the material FR4.

3. Measurement device according to claim 1, characterised in that the substrate (4) is a FR4 substrate.

4. Measurement device according to claim 1, characterised in that the sensor element (5) is a pressure sensor or a combined pressure and temperature sensor.

* * * * *